(12) United States Patent
Fägerman

(10) Patent No.: US 6,410,445 B1
(45) Date of Patent: Jun. 25, 2002

(54) MANUFACTURING METHOD FOR INTEGRATED SENSOR ARRAYS

(75) Inventor: Per-Erik Fägerman, Linghem (SE)

(73) Assignee: Appliedsensor Sweden AB (SE)

( * ) Notice: Subject to any disclaimer, the term of this patent is extended or adjusted under 35 U.S.C. 154(b) by 0 days.

(21) Appl. No.: 09/491,020

(22) Filed: Jan. 25, 2000

(30) Foreign Application Priority Data

Jan. 25, 1999 (SE) .............................................. 9900239

(51) Int. Cl.[7] .......................................... H01L 21/311
(52) U.S. Cl. ........................................ 438/695; 438/49
(58) Field of Search ............................... 438/695, 697, 438/680, 10, 11, 12, 17, 37, 49, 50; 430/311, 312

(56) References Cited

U.S. PATENT DOCUMENTS

| | | | |
|---|---|---|---|
| 2,857,251 A | 10/1958 | Krogh | 23/232 |
| 3,595,621 A | 7/1971 | Andreatch | 23/254 E |
| 4,169,126 A | 9/1979 | Iles | 422/95 |
| 4,321,322 A | 3/1982 | Ahnell | 435/34 |
| 4,584,867 A | 4/1986 | Forster | 73/23 |
| 4,875,083 A | 10/1989 | Palmour | 357/23.6 |
| 4,885,929 A | 12/1989 | Kasahara et al. | 73/23 |
| 4,897,162 A | 1/1990 | Lewandowski et al. | 204/1 T |
| 4,992,384 A | 2/1991 | Laurs et al. | 436/151 |
| 5,264,383 A | * 11/1993 | Young | 438/151 |
| 5,285,084 A | 2/1994 | von Windheim et al. | 257/77 |
| 5,296,125 A | * 3/1994 | Glass et al. | 204/153.21 |
| 5,323,022 A | 6/1994 | Glass et al. | 257/77 |
| 5,332,681 A | 7/1994 | Tonucci et al. | 437/16 |
| 5,545,377 A | 8/1996 | Fukaya et al. | 422/108 |
| 5,691,215 A | 11/1997 | Dai et al. | 437/44 |
| 5,693,877 A | 12/1997 | Ohsuga et al. | 73/118.1 |
| 6,109,094 A | 8/2000 | Baranzahi et al. | 73/31.06 |

FOREIGN PATENT DOCUMENTS

| | | | |
|---|---|---|---|
| CH | 665908 | 6/1988 | G01N/27/14 |
| DE | 3151891 | 7/1983 | G01N/27/12 |
| EP | 305963 | 3/1989 | G01N/31/10 |
| EP | 488352 | 6/1992 | G01N/27/12 |
| EP | 492700 | 7/1992 | G01N/27/414 |
| EP | 557642 | 9/1993 | G01N/33/02 |
| GB | 2127977 | 4/1984 | G01N/27/28 |
| SE | 503265 | 9/1994 | G01N/27/12 |
| WO | WO 96/09534 | 3/1996 | G01N/27/22 |
| WO | WO 00/75649 | 12/2000 | G01N/27/414 |

OTHER PUBLICATIONS

Schweizer–Berberich et al, Characterisation of food freshness with sensor arrays, Sensors and Actuators, B 18–19, (1994) pp. 282–290.

Di Natalie et al, "Multicomponent analysis on polluted waters by means of an electronic tongue", Sensors and Actuators B 44 (1997) pp. 423–428.

Legin et al, "Tasting of beverages using an electronic tongue" Sensors and Actuators B44 (1997) pp. 291–296.

* cited by examiner

Primary Examiner—Matthew Smith
Assistant Examiner—Calvin Lee
(74) Attorney, Agent, or Firm—Hayes Soloway P.C.

(57) ABSTRACT

Method for the fabrication of sensor arrays with individually different sensing surface, where lift off technique and shadow mask technique is used simultaneously. A resist layer with openings at all locations where coatings are intended is applied with lift off technique. Then a shadow mask is used provided with widows only at the openings where deposit is intended for one specific coating. By for instance vapor deposition, coatings are effected where there are openings in the resist and windows in the shadow mask. The shadow mask is moved to the next depositions location and the procedure repeated until all coatings have been effected. The shadow mask is removed as is also the resist giving an improved sensor quality compared to prior-art methods.

11 Claims, 2 Drawing Sheets

MANUFACTURING METHOD FOR INTEGRATED SENSOR ARRAYS

TECHNICAL FIELD

The present invention relates to a method for manufacturing integrated arrays of sensors, in particular chemical sensors or physical sensors e.g., field-effect chemical sensors. Such sensors are typically based on metal-insulator-semiconductor or metal-conductor structures. The present invention improves the quality of the top layer that serves as the chemically sensitive part of the device.

1. Introduction

It is known that catalytic metals can be used as gate electrodes for chemically sensitive field-effect devices such as transistors, capacitors, diodes, etc. These metal-insulator-semiconductor or metal-semiconductor devices may be used to measure small concentrations of molecules in the gas phase or ions in the liquid phase. The parameters that are normally changed when manufacturing field-effect sensors with different sensitivities towards different chemical compounds are the material and thickness of the top electrode. In this way the individual sensors in an array can be made sensitive to different compounds as well as differently sensitive to the same compound increasing the accuracy in the detection. There is an increasing need for arrays of chemical sensors with different chemical sensitivity patterns, e.g., for use in so-called electronic noses. Field-effect chemical sensors have the advantage that they can be manufactured using standard production methods for integrated electronic devices. Thus, it is possible to manufacture small and cheap arrays of field effect sensors with different chemical sensitivities on the same chip simply by using different top layers. In order to minimize the production costs of the devices, the arrays should be made with as small separation as possible between individual sensors. It is also very important that the to player electrodes, which can have a thickness down to some nanometers, are deposited with a high lateral precision, purity, and uniformity to achieve a good reproducibility and high quality sensors.

2. Prior art

The deposition of the top-layer electrodes on field-effect chemical sensors is made either using standard lift-off techniques or using shadow-mask techniques. A lift-off procedure typically includes the following steps: deposition of the resist, masking, exposure, and developing of the resist to create openings in the resist, deposition of the sensor top-layer material, and cleaning and rinsing of the surface to remove the resist. This entire procedure has to be done once for each type of top-layer material in the array, meaning that the sensing surfaces will be subjected to a number of lift-off procedures. Each lift-off procedure is, however, associated with a risk of contaminating the to player electrode or its substrate with small amounts of remaining resist. The result is impaired adhering between the deposited top layer and the substrate as well as contaminated top layers. Since the top layer controls the specific sensitivities of the sensor this seriously impairs the sensors recognizing ability. One way of circumventing this is to use very strong resist removers, but this instead increases the risk that the top-layer electrode peels off.

By instead using shadow-mask techniques, the problems associated with lift-off are avoided since no resist layers have to be processed and removed. Instead a precision-machined mask of some suitable material is used to define the top layer or electrode areas instead of the patterned resist mask. However, the shadow-mask technique is much less accurate than lift-off procedures and thus requires an unnecessary large electrode area and separation between individual sensors. Furthermore, the shadow-mask technique requires a complicated manual positioning step for each type of top layer, making it more time-consuming and expensive than lift-off procedures. Also the edges of the applied areas will be less precisely shaped resulting in variations between the different sensors.

THE INVENTION

The object of the invention is to eliminate the above problems to obtain a fabrication method giving the desired quality, control and repeatability. In accordance with the present invention, there is provided a method for fabricating integrated sensor arrays on a common substrate, comprising a first step of developing a resist mask on the surface of the substrate, wherein the resist mask is provided with openings for all areas of the substrate where a deposition is to take place in subsequent steps. Then, a first shadow mask is located over the resist mask from the first step and a first deposition of materials takes place in which the first shadow mask screens and protects all openings in the resist mask that are not to be subject to deposition leaving only those where the deposition is to take place. Thereafter, a second shadow mask is located over the resist mask and a second deposition takes place in areas of the openings in the resist mask on the substrate that are not screened by said second deposition. Additional shadow masks then are used to expose the desired openings in the resist mask to a treatment, and, after all depositions have been carried out a different openings in the resist mask, the last shadow mask is removed and then the resist mask is removed. Further advantageous improvements of the method are described in the following description of a preferred embodiment described with reference to the enclosed drawings wherein like numerals depict like parts, and wherein:

DESCRIPTION OF EMBODIMENT OF THE INVENTION

Step 1. The entire substrate wafer is subjected to the first part of a single lift-off procedure resulting in a resist layer with openings for all the top-layer sensor surfaces where the sensing layer material is to be deposited.

Step 2. The wafer is additionally covered by a shadow mask with only one mask window for each sensor of a first type in the array. The windows are larger than the resist openings and the windows are situated so that the mask can be placed with one window over each opening in the resist where deposition of a layer of a first type is intended (note that there can be more than one sensor of the same type in each array). The first material is deposited, e.g., by evaporation or sputtering in a vacuum chamber.

Figure 1:
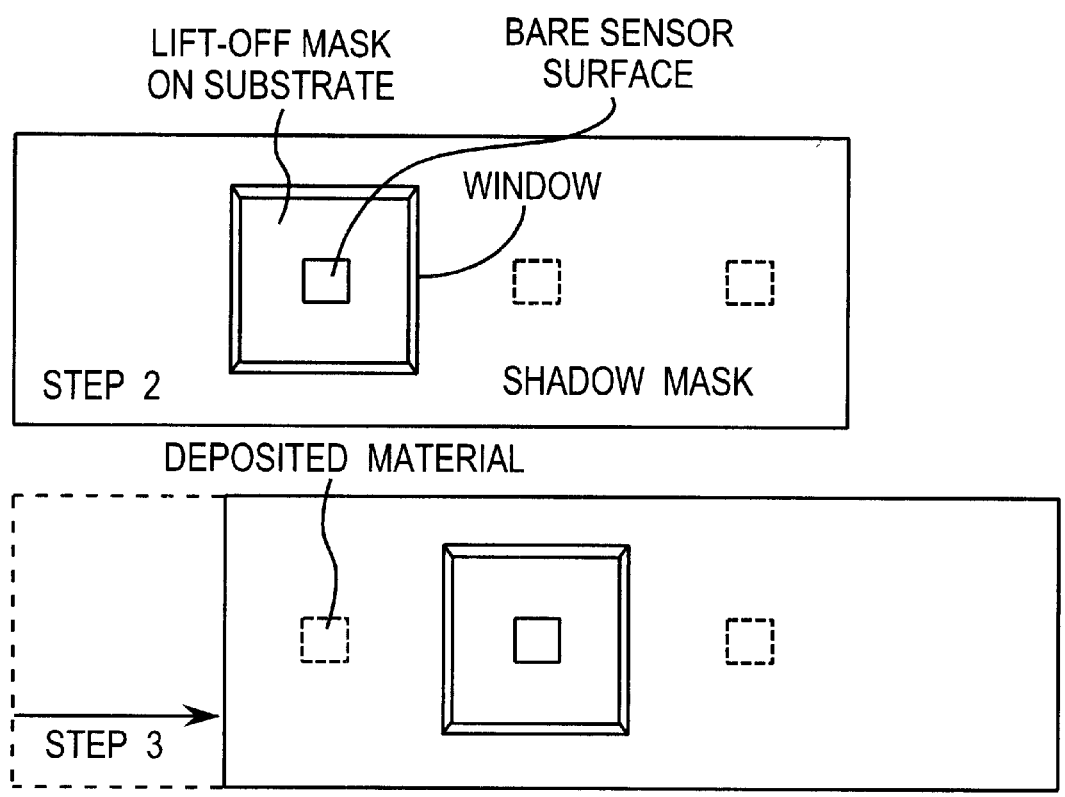
FIG. 1 is a schematic flow diagram of the process of the present invention.
Figure 2:
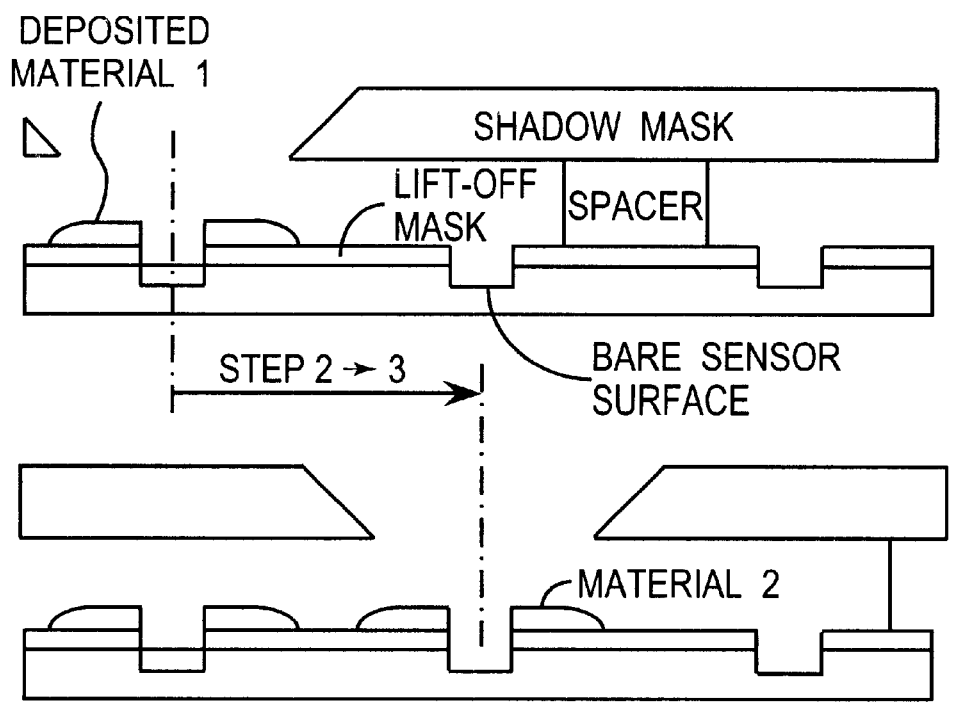
FIG. 2 is a cross-sectional view illustrating a mask made in accordance with the present invention.

Step 3. The shadow mask is then moved so that its windows are located where a second type of sensor may be located in the array (see FIGS. 1 and 2). Then the next or second electrode material is deposited in and close to the openings in the resist.

Step 3 is repeated until all sensor types are covered with to player electrodes.

Step 4. In a final step the shadow mask is removed and then the lift-off mask (resist) is removed with standard methods over the entire wafer.

Using the procedure described above, the top-layer electrode surfaces are never exposed to resist and they are only subjected to one single resist-removing procedure. The lateral precision and uniformity of the electrodes, however, are equally good as for a standard lift-off procedure but with the advantage of the shadow mask method, namely that the deposited materials remain pure and unaffected and with improved adhering.

In the above-described embodiment the shadow mask is displaced one step corresponding to the sensor spacing between each coating step. Instead different shadow masks can be used provided with guides locating themselves relative to the wafer.

In order to allow rapid work, the shadow mask should preferably be provided with a distance element holding it a small distance over the resist. Preferably the distance element or elements comprise a highly porous layer arranged on the side of and, if desired, adhered to the shadow mask, facing the resist mask and the substrate at deposition. Without a distance element the shadow mask will together with the openings in the resist that are covered by the mask constitute enclosures from which it may take some time before the air is evacuated. Either the air impairs the deposition or it slows down the depositing. Additionally said enclosures can also retain the vacuum when the pressure is increased holding the shadow mask pressed against the resist and wafer, so that it may become damaged if moved even slightly. Here it may take some considerable time before the shadow mask is free to be moved.

Improvements by the Invention

The invention reduces the number of necessary lift-off steps to only one, which means that all the bare sensor surfaces (i.e., the surfaces prior to deposition of the top-layer electrode) are only subjected to one deposition of the resist In prior art, the bare sensor surfaces were subjected to a number of lift-off procedures, varying from one procedure up to the same number as there are sensor types in the array. This resulted in a large risk of contaminating the bare sensor surface prior to the final deposition of the top-layer electrode.

Using the invention, the top-layer electrodes are never covered by resist and only subjected to one resist-removing step. This reduces the risk of peeling off or contaminating the top-layer electrode as compared to the prior-art lift-off method.

In comparison with prior-art shadow mask techniques, the invention allows a more dense packing of the sensors, which results in a lower production cost for each sensor array. Furthermore, even with a lowquality shadow mask the invention gives a higher lateral precision and uniformity of the top-layer electrodes than can be achieved using prior art with highquality shadow masks.

In summary, this invention combines the best features of the lift-off masking method and the shadow-mask method and minimizes the negative effects of each of these methods.

The above described technique can be used for the coating of sensors with different materials and/or different thickness and even multilayer coatings of different materials that vary between the individual sensors. The invention is further applicable for small series as well as industrialized processes.

What is claimed is:

1. A method for fabricating integrated sensor arrays on a common substrate, comprising a first step of developing a resist mask on the surface of the substrate, wherein the resist mask is provided with openings for all areas of the substrate where a deposition is to take place in subsequent steps; a second step in which a first shadow mask is located over the resist mask from the first step and a first deposition of materials takes place in which the first shadow mask screens and protects all openings in the resist mask that are not to be subjected to deposition leaving only those where the deposition is to take place; a third step in which a second shadow mask is located over the resist mask and a second deposition takes place in areas of the openings in the resist mask on the substrate that are not screened by said second deposition; subsequent steps in which additional shadow masks are used to expose the desired openings in the resist mask to a treatment; and a last step in which after all depositions have been carried out at different openings in the resist mask the last shadow mask is removed and then the resist mask is removed.

2. Method according to claim 1, wherein the windows in the shadow mask are sufficiently large to give a deposition extending over an area that is larger than the openings in the resist mask.

3. Method according to claim 1, wherein different shadow masks are used for different depositions.

4. Method according to claim 1, wherein the shadow mask is displaced between depositions.

5. Method according to claim 1, wherein a distance element is arranged between the shadow mask and the resist.

6. Method according to claim 1, wherein the sensor is a chemical sensor.

7. Method according to claim 6, wherein the sensor is a field-effect chemical sensor.

8. Shadow mask for use with the method according to claim 1, wherein the mask is provided with distance elements on the side facing resist mask and the substrate when used.

9. Shadow mask according to claim 8, wherein the distance elements comprise protrusions on the side of the shadow mask facing the resist mask and the substrate at deposition.

10. Mask according to claim 8, wherein the distance elements comprise a highly porous layer arranged on the side of the shadow mask facing the resist mask and the substrate at deposition.

11. Mask according to claim 10, wherein the porous layer is adhered to the shadow mask.

* * * * *